US012697113B2

(12) United States Patent     (10) Patent No.:   US 12,697,113 B2

Dooney, Jr. et al.     (45) Date of Patent:     Aug. 4, 2026

(54) ROTATOR CUFF REPAIRS AND RECONSTRUCTIONS

(71) Applicant: ARTHREX, INC., Naples, FL (US)

(72) Inventors: Thomas Dooney, Jr., Naples, FL (US); Matthew T. Provencher, Basalt, CO (US); Trevor D. Arnold, Naples, FL (US)

(73) Assignee: ARTHREX, INC., Naples, FL (US)

( * ) Notice: Subject to any disclaimer, the term of this patent is extended or adjusted under 35 U.S.C. 154(b) by 594 days.

(21) Appl. No.: 17/935,649

(22) Filed: Sep. 27, 2022

(65) Prior Publication Data

US 2024/0099752 A1     Mar. 28, 2024

(51) Int. Cl.
    *A61B 17/04*     (2006.01)
    *A61F 2/08*     (2006.01)

(52) U.S. Cl.
    CPC ...... *A61B 17/0466* (2013.01); *A61B 17/0401* (2013.01); *A61F 2/0811* (2013.01)

(58) Field of Classification Search
CPC .. A61F 2/0811; A61F 2/08; A61F 2002/0852; A61B 17/0401; A61B 17/0466; A61B 2017/0464; A61B 17/0469
See application file for complete search history.

(56) References Cited

U.S. PATENT DOCUMENTS

| | | | |
|---|---|---|---|
| 2007/0191849 A1* | 8/2007 | ElAttrache | ......... A61B 17/0401 606/326 |
| 2008/0188936 A1* | 8/2008 | Ball | ......................... A61F 2/08 623/13.13 |
| 2017/0143551 A1* | 5/2017 | Coleman | ............ A61B 17/0482 |

\* cited by examiner

*Primary Examiner* — Katherine M Shi

(74) *Attorney, Agent, or Firm* — Potomac Law Group, PLLC

(57) ABSTRACT

Surgical constructs, assemblies, and methods for rotator cuff reinforcement are disclosed. Side tissue of a reconstructed rotator cuff is secured with at least one flexible coupler and at least one fixation device secured to bone.

12 Claims, 7 Drawing Sheets

100k

188k

90

100l

188l

90

ROTATOR CUFF REPAIRS AND RECONSTRUCTIONS

BACKGROUND

The disclosure relates to the field of surgery and, more specifically, to surgical constructs and tissue repairs for reconstructive surgeries.

SUMMARY

High-strength surgical constructs and methods of tissue repairs are disclosed. A surgical construct can include a repaired or reconstructed rotator cuff. A surgical construct can include unrepaired tissue on the sides of the rotator cuff which is repaired or reconstructed with the use of additional flexible couplers and fixation devices such knotless suture anchors. A surgical construct can be knotted or knotless.

A flexible coupler can extend between a reconstructed rotator cuff and unrepaired rotator cuff sides. A flexible coupler can include at least one flexible strand located over, around, under and/or through the unrepaired rotator cuff sides and forming one or more suturing passes over or through unrepaired rotator cuff sides, to stitch up the rotator cuff and reinforce it. A surgical construct can include at least one fixation device for providing at least one anchoring point of the unrepaired rotator cuff sides. A surgical construct can include one or more flexible couplers to reinforce the rotator cuff and/or repair the rotator cuff unrepaired side tissue. A surgical construct can be knotless, self-locking, and tensionable.

Methods of knotless, tensionable tissue repairs are also disclosed. A surgical construct provides knotless tissue to bone fixation, without knot formation, with increased fixation and improved healing, and uniform soft tissue compression, eliminating unrepaired tissue sides of a reconstructed tissue. A tissue can be rotator cuff tendon.

DETAILED DESCRIPTION

Figure 1:
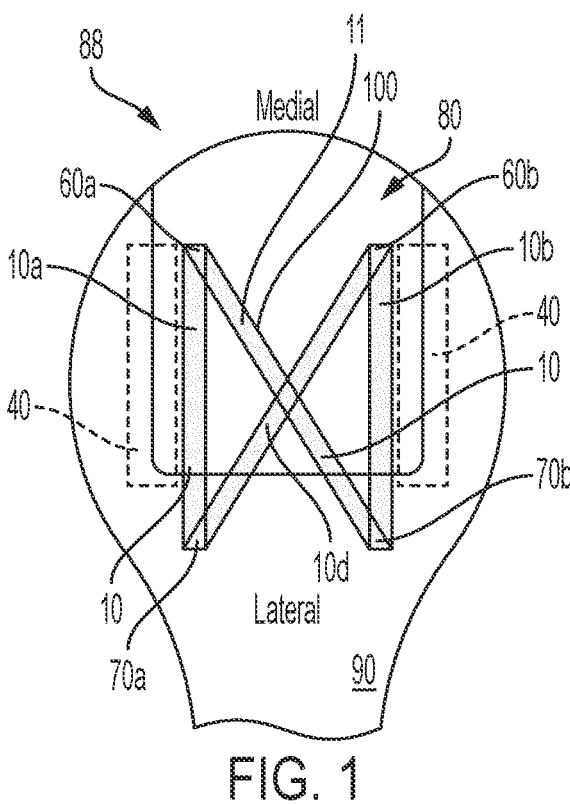
FIGS. 1-4 illustrate steps of a tissue repair.

The disclosure provides surgical systems, assemblies, constructs, and methods for tissue repairs and reconstructions. Side tissue located on sides of a reconstructed anatomical structure or tissue is reinforced with a flexible coupler and fixation devices. The flexible coupler can be suture, tape, weave, or mesh, among many others. The side tissue can be reinforced with the flexible coupler and fixation devices alone or in combination with any additional biological construct, for example, graft, collagen, collagen patch, and/or biological materials. The tissue can be the rotator cuff tendon. The side tissue can be attached to any fixation device(s), for example, knotted or knotless suture anchors. The surgical systems, assemblies, and constructs can be knotless. The surgical systems, assemblies, and constructs can be tensionable.

In an embodiment, a surgical construct can include side tissue of a repaired rotator cuff. Part or all of the side tissue is secured with at least one flexible coupler and one or more fixation devices such as knotless suture anchors. The flexible coupler can be suture or tape, for example, suture tape. The flexible coupler can be provided over, under, around and/or through the rotator cuff side tissue by forming, for example, a stitched region including one or more suture passes over the rotator cuff sides. A surgical construct can be knotless, self-reinforcing, tensionable, adjustable.

A surgical assembly or surgical system can include a repaired (reconstructed) rotator cuff; at least one flexible coupler provided over and/or through unrepaired sides of the rotator cuff; and at least one fixation device attached to the at least one flexible coupler. The surgical assembly can optionally include a reinforcement material (for example, graft, collagen, collagen patch, biological materials) provided along at least one dimension (for example, the width) of the rotator cuff, to aid in providing a reinforced rotator cuff. The at least one fixation device can be an anchor, button, implant, screw, plate, suture loop/button construct, or combinations thereof. The at least one fixation device can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein. A knotless fixation device comprises an anchor body (or screw) and an eyelet.

A reinforced rotator cuff can include a sutured or stitched region formed by employing (1) a flexible coupler; and conducting (2) at least one pass over and/or through unrepaired side tissue of the rotator cuff. The step of conducting (2) at least one pass over and/or through the unrepaired side tissue could take place after or before the rotator cuff tendon has been reconstructed. The flexible coupler can be passed over and/or through at least a portion of side tissue to reinforce the rotator cuff. The flexible coupler can be passed over and/or through the whole length of the side tissue to reinforce the rotator cuff. The flexible coupler can be attached/secured to the side tissue by suturing (for example, stitching) or by any other affixing/attachment techniques, to provide additional reinforcement. A reinforced rotator cuff construct can further include an additional reinforcing/reinforcement material. The reinforced rotator cuff construct and/or the additional reinforcing/reinforcement material can be attached to additional fixation devices such as knotless anchors. The fixation devices can provide additional fixation to bone. The reinforced construct can be knotless, self-locking, tensionable.

Methods of forming knotless, reinforced rotator cuff constructs having increased pull-out strength as well as methods of reinforcing a rotator cuff are also disclosed. An exemplary method of forming a knotless, reinforced rotator cuff construct (reinforced rotator cuff) comprises: (i) securing rotator cuff side tissue with at least one flexible coupler; and (ii) fixating the at least one flexible coupler with at least one fixation device to form a reinforced rotator cuff. The at least one flexible coupler can be any strand or fiber that can allow suturing/stitching around an outer perimeter of the rotator cuff side tissue and along at least one dimension of the rotator cuff (for example, along its anterior and/or posterior sides or edges). The at least one flexible coupler can be secured to parts of the rotator cuff that has been already reconstructed (not side tissue) and then passed over the rotator cuff side tissue. The at least one flexible coupler can be also passed over and/or through at least a portion of the rotator cuff side tissue. The at least one flexible coupler can be suture or suture tape, among many others. The fixation device can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein.

The surgical constructs provide knotless systems and novel ways to repair large soft tissue tears where only certain attachment points are fixated back to bone. In an exemplary embodiment, the disclosure provides knotless fixation of rotator cuff to bone, without knot formation, with fewer passing steps, increased fixation and reinforcement, uniform rotator cuff compression, and overall rotator cuff rehabilitation and repair.

The side repair sutures can be connected to the medial-lateral sutures before or after the lateral anchor fixation. The side repair anchors can be either under or not under the soft tissue. The side repair sutures can be: luggage tag; through the suture (pierced through or through a premade eyelet); around the suture; pre-attached to the suture; or combinations thereof.

Referring now to the drawings, where like elements are designated by like reference numerals, FIGS. 1-14 illustrate exemplary tissue repairs 100a; 100b; 100c; 100d; 100e; 100f; 100g; 100h; 100i; 100j; 100k; 100l (rotator cuff side repair 100a; 100b; 100c; 100d; 100e; 100f; 100g; 100h; 100i; 100j; 100k; 100l; or RCR side fix 100a; 100b; 100c; 100d; 100e; 100f; 100g; 100h; 100i; 100j; 100k; 100l; or double row RC—side repair 100a; 100b; 100c; 100d; 100e; 100f; 100g; 100h; 100i; 100j; 100k; 100l) with reconstructed reinforced rotator cuff 188a; 188b; 188c; 188d; 188e; 188f; 188g; 188h; 188i; 188j; 188k; 188l.

The exemplary tissue repairs detailed below are rotator cuff repairs. However, the disclosure is not limited to these exemplary-only embodiments and it must be understood that the present disclosure encompasses any tissue repair which involves side tissue of a repaired/reconstructed anatomical construct. Thus, surgical constructs and repair methods detailed below have applicability not only to rotator cuff repairs, but also to surgical procedures such as Achilles tendon repair, patellar tendon repair, ACL/PCL reconstruction, hip and shoulder reconstruction procedures, and applications for suture used in or with suture anchors. The surgical constructs and repair methods of the present disclosure can be employed in tissue repairs that do not involve knot tying, for example, for use with suture anchors (such as PushLock® and/or SwiveLock® suture anchors) or for knotless arthroscopic suture repairs (such as knotless single row rotator cuff repair, or SpeedBridge™ repairs using no knots and only suture passing steps), among many others.

FIG. 1 illustrates a schematic rotator cuff 80 (tissue 80; soft tissue 80; rotator cuff tendon 80) secured over bone 90.

FIG. 1 also illustrates placement of first and second medial fixation devices 60a, 60b (medial fixation devices 60a, 60b) and first and second lateral fixation devices 70a, 70b (lateral fixation devices 70a, 70b) and with at least one flexible coupler 10 extending in between to reconstruct rotator cuff 80 and form reconstructed rotator cuff 88. In an exemplary embodiment, any of fixation devices 60a, 60b, 70a, 70b can be an anchor (knotted anchor, knotless anchor, or all-suture anchor), implant, button, screw or any fixation device that confers secure attachment and fixation of the rotator cuff 80 over bone 90. The fixation device 60a, 60b, 70a, 70b can be a knotless suture anchor such as a two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of both of which are fully incorporated by reference in their entirety herein.

At least one flexible coupler 10 can be placed in locking configuration and incorporated with anchor placement. Flexible coupler 10 can be formed of any flexible material. In an embodiment, flexible coupler 10 is round suture. In an embodiment, flexible coupler 10 is FiberWire® suture. In an embodiment, flexible coupler 10 is a tape such as suture tape. In an embodiment, flexible coupler 10 is FiberTape® suture tape.

FIG. 1 also illustrates unrepaired tissue/sides 40 of rotator cuff 80, i.e., unrepaired tissue 40 that remains untreated/unsecured/unfixed/unattached after the repair of the rotator cuff 80. Unrepaired tissue 40 extends along sides of reconstructed rotator cuff 88, for example, alongside suture passes 10a, 10b of suture mattress 11.

Reconstructed rotator cuff 88 can be formed by any method known in the art. In exemplary embodiments only, reconstructed rotator cuff 88 can be formed by repairs that do not involve knot tying, for example, for use with suture anchors (such as PushLock® and/or SwiveLock® suture anchors) or knotless arthroscopic suture repairs (such as knotless single row rotator cuff repair, or SpeedBridge™ repairs using no knots and only suture passing steps), among many others.

An exemplary SutureBridge™ tendon repair technique, developed by Arthrex, Inc., and disclosed in U.S. Pat. No. 8,012,174 (the disclosure of which is herein incorporated by reference in its entirety) consists of a tied medial row constructed with two threaded suture anchors 60a, 60b, combined with knotless lateral fixation using two Arthrex PushLocks® constructs 70a, 70b. The construct enhances footprint compression and promotes tendon healing-to-bone with minimal knot tying.

An exemplary SpeedBridge™ technique, also developed by Arthrex, Inc., and disclosed in U.S. Pat. No. 9,005,246 (the entire disclosure of which is herein incorporated by reference) uses a threaded swivel anchor combined with FiberTape® suture tape to create a quick and secure Suture-Bridge™ construct with no knots and only two suture passing steps. In the SpeedBridge™ technique, a swivel anchor 60a, preferably an Arthrex 4.75 mm SwiveLock® C 60a, loaded with one strand of FiberTape® suture tape 10, is inserted into a medial bone socket. A suture shuttle such as FiberLink™ may be used to shuttle both FiberTape® tails through the rotator cuff 80 simultaneously. A FiberLink™ tail is passed through the rotator cuff using a suture passing instrument such as the Scorpion™. The tails of the Fiber-Tape® suture tape are loaded through the FiberLink™ loop and shuttled through the rotator cuff 80. These steps are repeated for the second medial row anchor 60b. The final repair is provided with unrepaired tissue 40 (dog ears 40) alongside reconstructed rotator cuff 88.

A method of double row fixation of tendon 80 to bone 90 to form reconstructed rotator cuff 88 as detailed in U.S. Pat. No. 8,012,174 comprises inter alia the steps of: (i) attaching first flexible strand 10 (FiberTape® suture tape with limbs 10a, 10c) to a fixation device 60a (for example, a knotless fixation device or a soft anchor) and attaching second flexible strand 10 (FiberTape® suture tape with limbs 10b, 10d) to a fixation device 60b (for example, a knotless fixation device or a soft anchor); (ii) securing the fixation device 60a, 60b into bone 90 while limbs of the first and second flexible strand 10 (FiberTape® suture tape limbs) are positioned over soft tissue 80; and (iii) securing limbs 10a, 10b, 10c, 10d (FiberTape® suture tape limbs) with lateral fixation devices 70a, 70b (for example, a knotless fixation device or a soft anchor) into bone 90. The method may further comprise the step of securing the fixation devices into a bone socket or tunnel or pushing the fixation devices into bone without forming a bone socket or tunnel.

Figure 2:
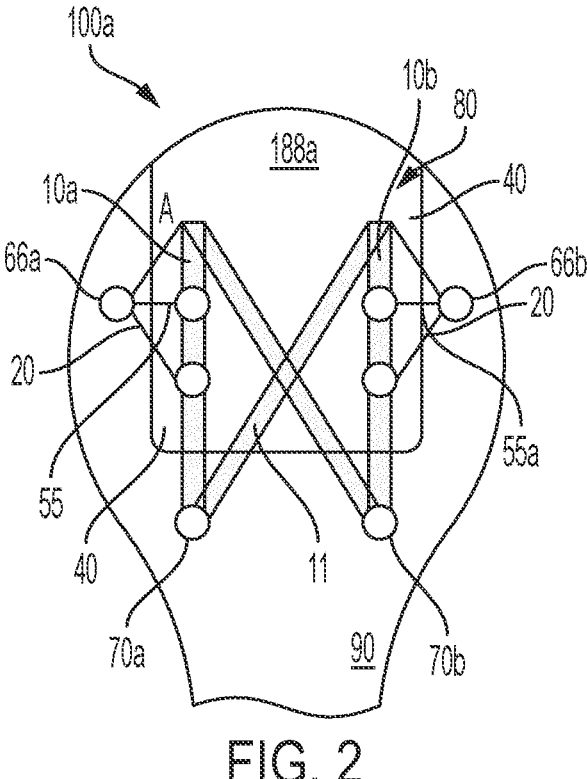

FIG. 2 illustrates exemplary repair 100*a* of the present disclosure. Side tissue 40 is fixed to the side with more compression and in a more anatomical way than fixing the side tissue to the lateral row.

Figure 4:
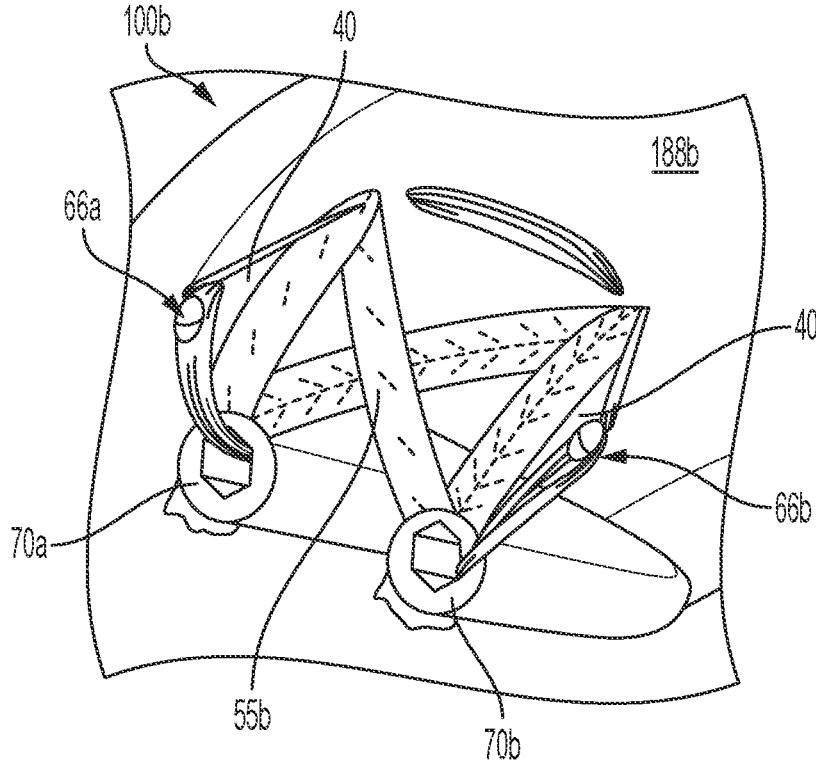

Typical rotator cuff (RC) repair constructs fix the tissue with suture bridging constructs going from the medial to the lateral. These RC repairs leave the tissue on the sides relatively "unrepaired." Exemplary repairs 100*a*, 100*b* of FIGS. 2 and 4 provide fixation methods to address and fixate the unrepaired tissue on the anterior and posterior sides of a RC repair and achieve reconstructed rotator cuff 188*a*, 188*b* with fixated side tissue 40.

Suture A of FIG. 2 can be any flexible coupler/strand leading from a medial row RC anchor (such as knotless fixation device 60*a*, 60*b*) to be inserted into a knotless suture anchor 66*a*, 66*b* (anterior and posterior suture anchors 66*a*, 66*b*) to fix the unrepaired tissue 40. Side tissue 40 can be secured with additional passes and/or stitches and/or fixation devices to reinforce the lateral sides of rotator cuff 80. For example, FIG. 2 illustrates two additional passes of flexible coupler 20 (suture 20) over each of side tissue 40 of the rotator cuff, reinforcing the rotator cuff 80. Any number of passes of flexible coupler 20 and any number of fixation devices can be employed for final repair 100. Although FIG. 2 shows only four fixation devices, it must be understood that any number of fixation devices can be employed on either side of the repair and with any number of additional flexible couplers and stitches, as desired and depending on the characteristics of each of the side tissue 40 on either way of the reconstructed rotator cuff 88.

FIG. 2 shows three suture passes/stitches with flexible coupler 20 (sutures A, B, C, D of FIG. 3) to form exemplary suturing pattern 55*a* on each side of the reconstructed rotator cuff 88. Multiple suturing methods may be achieved by integrating the coupler 20 in the final repair 100*a* (e.g., whipstitch, rip-stop, Krackow, baseball, loop and tack, Bunnell, Kessler, Bauer, Strobel, etc. repairs). Suturing pattern 55*a* may have any configuration and pattern as long as the unrepaired sides 40 of rotator cuff 80 are reinforced along at least a length of one or more of its dimensions, for example, along the side or anterior or posterior side/direction of the cuff, with the flexible coupler 20. A plurality of suturing passes can be provided from the anterior or posterior side to the fixation devices 66*a*, 66*b* (anterior and posterior fixation devices 66*a*, 66*b*) provide within bone 90. The suturing/stitching can be achieved from any direction and suture passes can be provided on any portion of the side tissue 40, or over/on the whole area of the side tissue 40.

Figure 3:
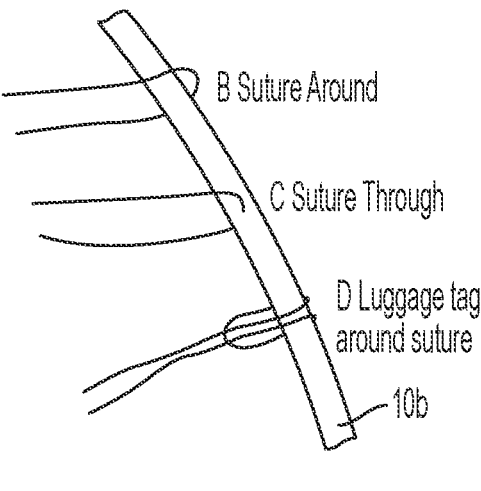

FIG. 3 illustrates additional embodiments of the present disclosure. Sutures B, C, D (flexible coupler 20) are options to help repair the tissue 40 and are passed around or through a medial-lateral suture repair limb (such as suture repair limb 10*a*, 10*b* of FIG. 1), prior to lateral anchor fixation. Once the lateral anchor 70*a*, 70*b* is fixated, these suture(s) can then be fixated with a knotless suture anchor (such as fixation devices 66*a*, 66*b*) alongside the repair. Sutures B, C, D can be also passed through or around the medial-lateral suture repair limb after lateral fixation is completed; however, since the medial-lateral suture repair limb should be tight and compressed against tissue 80, attachment of sutures B, C, D to this medial-lateral suture repair limb can be difficult after lateral fixation is completed and, thus, it is preferably conducted prior to lateral anchor fixation.

Suture B of FIG. 3 is passed around medial-lateral suture repair limb 10*b*. Suture C of FIG. 3 is passed through medial-lateral suture repair limb 10*b*. Suture D of FIG. 3 forms a luggage tag 15 around medial-lateral suture repair limb 10*b*. Single or multiple sutures (flexible strands) can be implanted alongside the repair. Single or multiple sutures (flexible strands) can be implanted alongside the repair to form at least one suture loop around medial-lateral suture repair limbs 10*a*, 10*b* and/or at least one stitch 20 over unrepaired sides 40 of rotator cuff 80, to reinforce the rotator cuff 80. It can be understood, however, that the flexible coupler 20 can also go around, under or through the rotator cuff 80, or all around, under and through it. A suture passer (suture passing instrument) such as Arthrex Scorpion™ Suture Passer or Arthrex SutureLasso™ may be employed to pass flexible coupler 20 (suture 20) around, under or through the medial-lateral suture repair limb 10*b*. In the illustrative embodiments, the flexible coupler 20 is passed around the medial-lateral suture repair limb 10*a*, 10*b* of the rotator cuff repair, to reinforce the rotator cuff without piercing it.

FIG. 4 illustrates exemplary repair 100*b* which fixates the unrepaired tissue 40 on the anterior and posterior sides of a RC repair to achieve reconstructed reinforced rotator cuff 188*b* with fixated side tissue 40. Flexible coupler 20 extends over the side tissue 40, connecting fixation devices 70*a*, 70*b* to fixation devices 66*a*, 66*b* all secured within bone 90 through mattress stich 55*b*. Fixation device 66*a*, 66*b* can be a knotless suture anchor such as the two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of all of which are fully incorporated by reference in their entirety herein.

Stitched/sutured/reinforced region 55*a*, 55*b* of the exemplary reinforced rotator cuff 188*a*, 188*b* can include a plurality of suture passes/stitches around an outer circumference of the rotator cuff. The stitched/sutured/reinforced region 55*a*, 55*b* may be formed in any manner, by conducting a plurality of suture passes from posterior to anterior or anterior to posterior, or from lateral to medial or medial to lateral. The stitched/sutured/reinforced region 55*a*, 55*b* may include any number of passes or stitches placed along at least a length of the reconstructed rotator cuff 188*a*, 188*b*. In an exemplary embodiment, a plurality of passes or stitches are placed along both sides of the rotator cuff 80, and in a direction about parallel to the longitudinal axis of the rotator cuff.

Exemplary fixations devices 60*a*, 60*b* can be two exemplary Arthrex SwiveLock® anchors 60*a*, 60*b* (for example, Arthrex 4.75-mm BioComposite SwiveLock® anchors) fixed to bone 90 (humerus 90). Each anchor can be provided with two tails (10*a*, 10*b*, 10*c*, 10*d*) and one limb (flexible coupler 20) which forms mattress or stitched/sutured/reinforced region 55*a*, 55*b*. FIG. 2 also shows additional suturing region 11 corresponding to the fixation devices 70*a*, 70*b* (suture anchors such as, for example, Arthrex 4.75-mm BioComposite SwiveLock® anchors) in a rip-stop pattern and by a SpeedFix™ or SpeedBridge™ configuration.

The SpeedFix™ and SpeedBridge™ techniques, both developed by Arthrex, Inc., use a threaded swivel anchor 70*a*, 70*b*, such as Arthrex SwiveLock® C anchor (disclosed and described in U.S. Pat. No. 8,012,174) combined with FiberTape® (disclosed in U.S. Pat. No. 7,892,256) to create a quick and secure SpeedFix™ construct (a knotless single row repair) or a SpeedBridge™ construct (a knotless double row repair) with no knots and very few suture passing steps.

In the SpeedFix™ technique, FiberTape® suture is passed in an inverted mattress using a SutureLasso™ or Scorpion™ suture passer. The two suture limbs of the mattress stitch can then be inserted into the SwiveLock® anchor eyelet. The loaded eyelet is inserted into a prepared lateral bone socket until the anchor body contacts bone, and the tension is adjusted if necessary. The SwiveLock® C driver is rotated in a clockwise direction to complete the insertion. Using an open ended FiberWire® cutter, the FiberTape® tails (10a, 10b, 10c, 10d) are cut to complete the technique.

Figure 5:
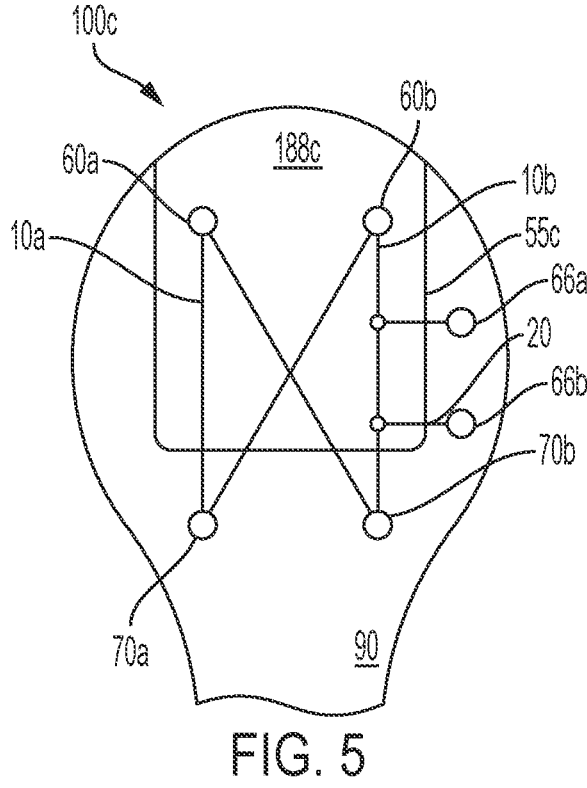
FIGS. 5-14 illustrate various tissue repairs.

FIGS. 5-14 illustrate additional soft tissue repairs of the present disclosure. One or more flexible couplers extend from and in between an exemplary reconstructed rotator cuff and unrepaired rotator cuff sides. FIG. 5 illustrates repair 100c wherein reconstructed rotator cuff 88 is reinforced by providing additional side repair sutures extending between side repair anchors and medial-lateral sutures to form reinforced rotator cuff 188c. As in the previous embodiments, the side repair sutures 20 can be connected to the medial-lateral sutures before or after the lateral anchor fixation 70a, 70b. FIG. 5 depicts a double row construct where the medial-lateral sutures have pre-assembled or pre-attached suture limbs connected (such as strand 20) that can go to the side, to form reinforced rotator cuff 188c.

Figure 6:
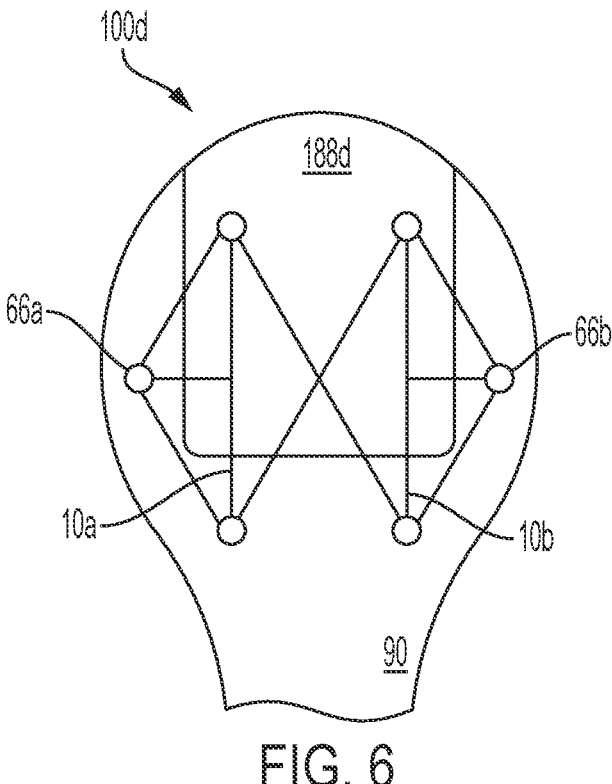

FIG. 6 illustrates repair 100d with reinforced rotator cuff 188d. The side repair suture can come from the medial side or medial anchor, middle of the suture, lateral side or lateral anchor.

Figure 7:
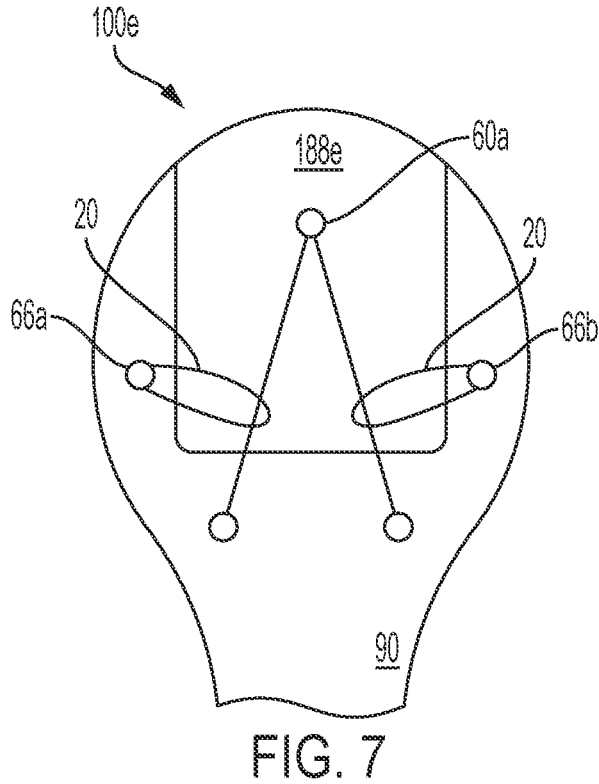

FIG. 7 illustrates repair 100e wherein the RC repair construct can have one or more medial anchors and one or more lateral anchors. For example, reinforced rotator cuff 188e includes only one medial anchor 60a. The medial to lateral suture can have multiple repair sutures 20 coming from them.

Figure 8:
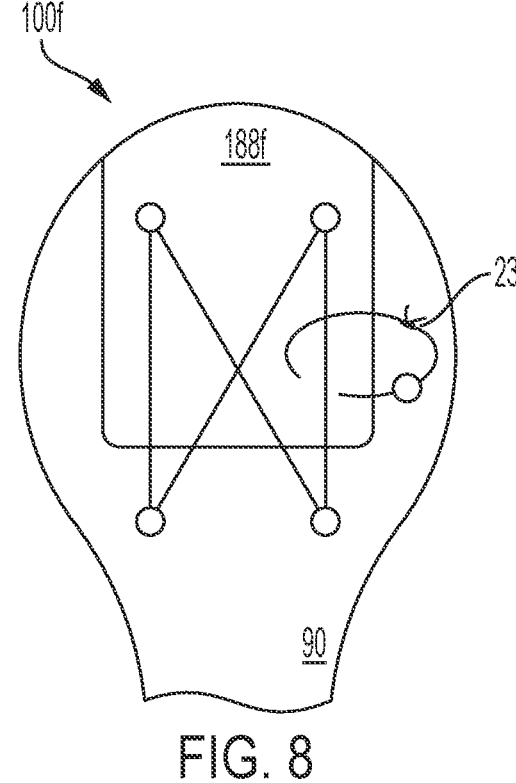

In other embodiment, the side repair suture can include a knot. For example, repair 100f of FIG. 8 shows reinforced rotator cuff 188f wherein the side repair is a knot tying anchor with knot 23 where the suture is passed under and around one of the medial-lateral sutures. The limb is then tied to its opposing suture from the anchor.

Figure 9:
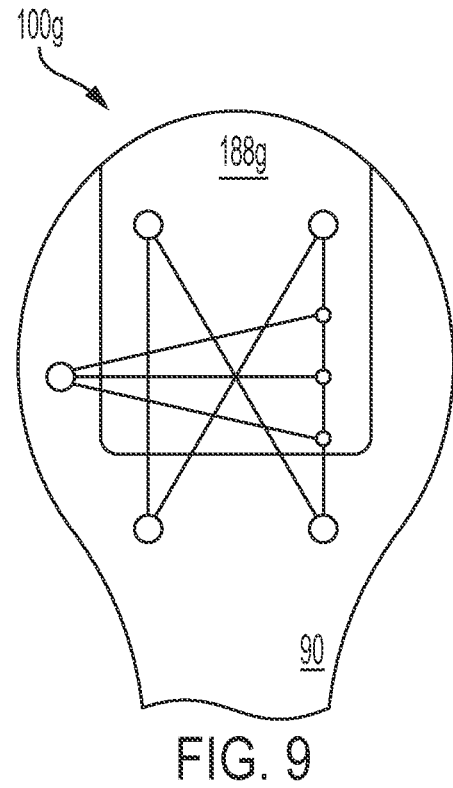
Figure 10:
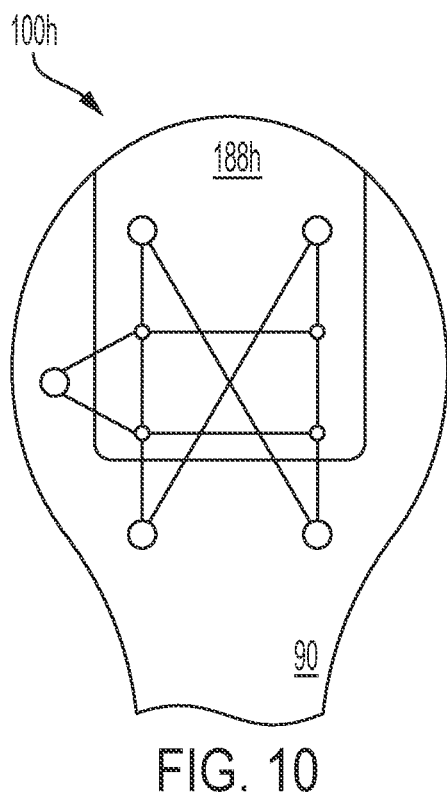
Figure 11:
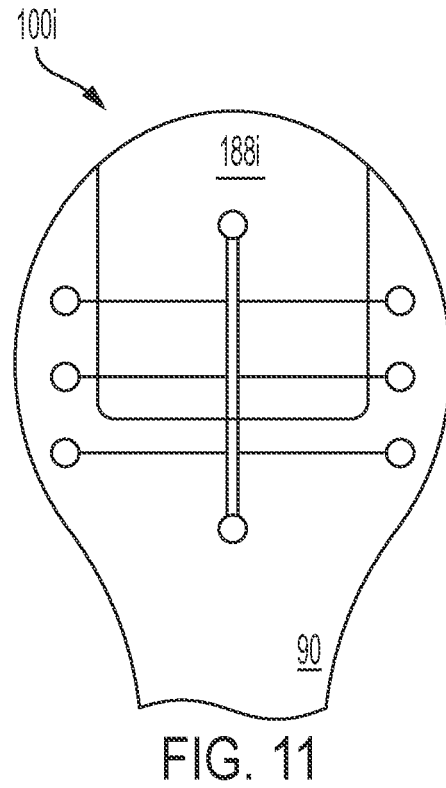
Figure 12:
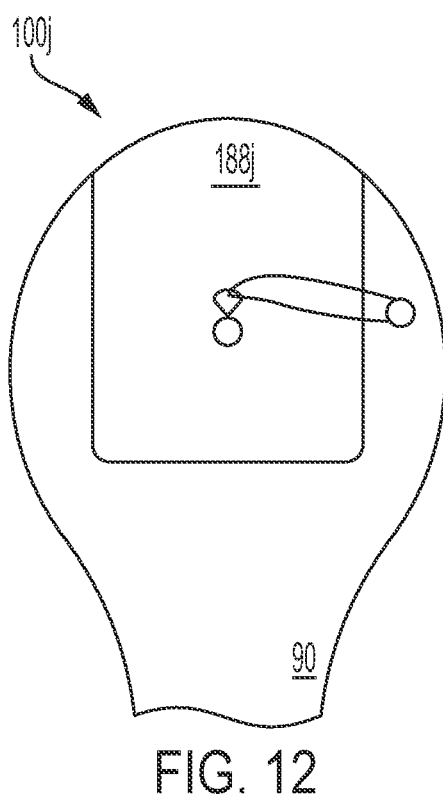

FIG. 9 illustrates reinforced rotator cuff 188g of repair 100g with side repair sutures going from an anterior suture to a posterior anchor, and vice-versa. FIG. 10 shows reinforced rotator cuff 188h of repair 100h wherein the side repair sutures could connect or go through multiple anchor sutures. FIG. 11 depicts reinforced rotator cuff 188i of repair 100i with at least one medial and one lateral anchor, to allow multiple repair sutures to be added. FIG. 12 shows repair 100j with reinforced rotator cuff 188j wherein a single anchor under the tissue can pass and secure the tissue with a mattress stitch. The side repair can be passed around the mattress stitch to complete the repair.

Figure 13:
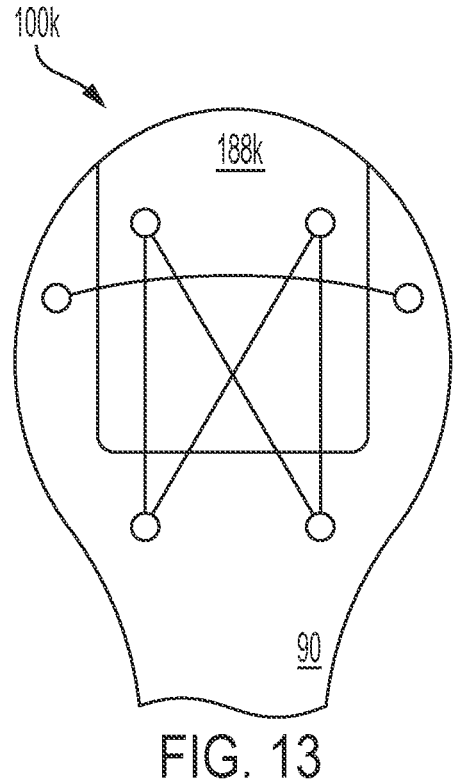
Figure 14:
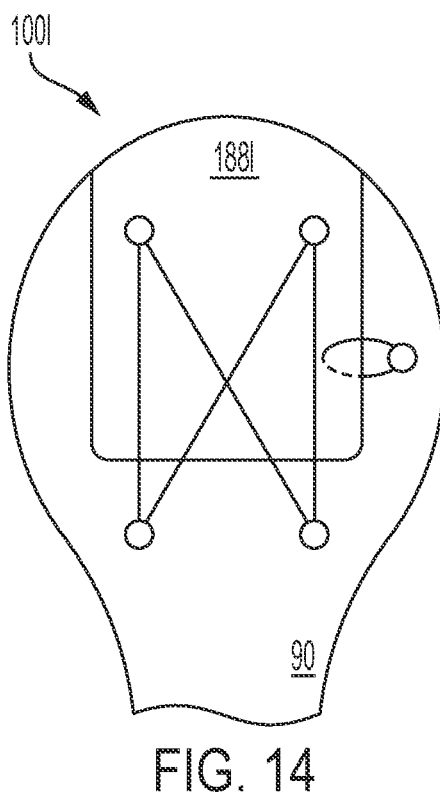

FIG. 13 depicts repair 100k with reinforced rotator cuff 188k. The side repair can be from one point to another independent of the tissue repair. A free horizontal suture is fixated from both sides. Reinforced rotator cuff 188l of repair 100l of FIG. 14 sows that the side repair can be completely independent of the primary cuff repair.

In the embodiments detailed above, the side repair sutures can be connected to the medial-lateral sutures before or after the lateral anchor fixation. The side repair anchors can be either under or not under the soft tissue. The side repair sutures can be: luggage tag; through the suture (pierced through or through a premade eyelet); around the suture; pre-attached to the suture; or combinations thereof.

In an exemplary embodiment, reconstruction of tissue 80 by repairs 100a; 100b; 100c; 100d; 100e; 100f; 100g; 100h; 100i; 100j; 100k; 100l may be conducted by employing fixation devices, wherein at least one of the fixation devices is a soft anchor or an "all-suture" anchor. A soft anchor (soft suture anchor or all-suture soft knotless anchor) is provided with a soft anchor sleeve (sheath or tubular member) with two open ends, and at least two flexible shuttling strands extending through the soft anchor sleeve (sheath). The flexible strands may extend through the sleeve in similar or different directions and/or orientations and/or locations. The flexible tubular sleeve with the shuttling strands may be secured into or onto bone, and flexible strands may pass over soft tissue (rotator cuff) and are secured into bone to approximate soft tissue to bone. Details of an exemplary soft suture anchor with a soft anchor sleeve (sheath or tubular member) and flexible shuttling strands are set forth, for example, in U.S. Pat. No. 10,849,734 issued Dec. 1, 2020, entitled "Methods of Tissue Repairs," the disclosure of which is incorporated by reference in its entirety herein.

A reinforced tissue construct 188a; 188b; 188c; 188d; 188e; 188f; 188g; 188h; 188i; 188j; 188k; 188l can include a stitched region (such as regions 55a, 55b) formed with at least one flexible coupler 20 passed at least once over, under and/or through unrepaired side tissue 40 of the reconstructed soft tissue 88 and secured to bone with at least one fixation device 66a, 66b. The flexible coupler 20 may be any strand, thread, fiber, yarn or similar structure, or plurality of such structures, that allows secure fixation of side tissue around the perimeter of the soft tissue and along at least a side of the soft tissue. The at least one fixation device 66a, 66b can be an anchor, implant, screw, button, plate, or any device that allows attachment of the flexible coupler 20 of the reinforced tissue construct 88 to bone 90. The fixation device 66a, 66b can be formed of metal, biocomposite materials, or can be an "all-suture soft anchor." The reinforced tissue construct 188a; 188b; 188c; 188d; 188e; 188f; 188g; 188h; 188i; 188j; 188k; 188l can be a knotless construct. The reinforced tissue construct 188a; 188b; 188c; 188d; 188e; 188f; 188g; 188h; 188i; 188j; 188k; 188l can be a knotted construct. The tissue construct can be rotator cuff.

A surgical assembly for tissue reinforcement comprises a flexible coupler 20 for knotless attachment to a reconstructed tissue 88; and at least one fixation device 66a, 66b attached to the flexible coupler. The at least one fixation device 66a, 66b can be a knotless suture anchor. The tissue can be rotator cuff.

A method of forming a reinforced, reconstructed rotator cuff construct 188a; 188b; 188c; 188d; 188e; 188f; 188g; 188h; 188i; 188j; 188k; 188l comprises inter alia the steps of: (i) attaching unrepaired sides 40 of reconstructed rotator cuff 88 to at least one flexible coupler 20; and (ii) securing the at least one flexible coupler 20 to bone 90. The flexible coupler 20 can be secured with at least one fixation device 66a, 66b. The flexible coupler 20 can be secured in a knotless manner. The at least one fixation device 66a, 66b can be an anchor, implant, screw, button, or plate. The at least one fixation device 66a, 66b can be a knotless suture anchor. The step of attaching unrepaired sides 40 can include passing the flexible coupler 20 with a suture passer around, under or through the rotator cuff side 40 multiple times to form at least one pass or at least one complete loop of suture over or around the rotator cuff side and as part of suturing/stitched region. In an embodiment, the flexible coupler 20 is passed multiple times to form a suturing/stitched region (such as region 55a, 55b) of a knotless suturing repair that provides for faster tissue reduction with a stronger and more reproducible repair. The method may further include the step of (iii) providing a reinforcement/reinforcing material (biological material) to augment the final repair. The method can be knotless.

Flexible coupler 10, 20 can be formed of any suture, tape, weave, fabric, ribbon, textile, web, or mesh, or any combinations of these materials. Flexible coupler 10, 20 can be braided or multi-filament suture such as FiberTape® suture tape (as disclosed in U.S. Pat. No. 7,892,256, the disclosure of which is incorporated in its entirety herewith) or collagen tape, or wide "tape like" material, or combinations thereof. Flexible coupler 10, 20 can be formed of a high strength suture material such as FiberWire® suture, sold by Arthrex, Inc. of Naples, Fla., and described in U.S. Pat. No. 6,716, 234, the disclosure of which is incorporated by reference herein. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material. Flexible coupler 10, 20 can be formed of any material or combination of materials that can be provided on or through a rotator cuff, along a length thereon, and stitched/sutured to provide additional fixation when the rotator cuff sides are further secured. The flexible coupler 10, 20 may be absorbable or non-absorbable.

Flexible coupler 10, 20 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible coupler 10, 20 can consist of strands with cross-sections of various forms and geometries, including round, oval, rectangular, or flat, among others, or combinations of such forms and geometries. In an embodiment, at least one of flexible coupler 10, 20 can be provided as a suture which is braided, knitted or woven.

Flexible coupler 10, 20 can be also formed of a stiff material, or combination of stiff and flexible materials, depending on the intended application. Flexible coupler 10, 20 can be also coated and/or provided in different colors. In an embodiment, parts (or all) of construct 88, 188, 288 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture and/or tape, pliability, handleability or abrasion resistance, for example.

Flexible coupler 10, 20 can be also provided with tinted tracing strands, or otherwise contrast visually with other parts of the construct, which remain a plain, solid color, or displays a different tracing pattern, for example. Various structural elements of the surgical constructs may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A rotator cuff reconstruction method comprising:
repairing a rotator cuff by attaching the rotator cuff to bone from medial to lateral and by employing at least one flexible strand and a plurality of medial and lateral fixation devices to form a repaired rotator cuff; and
securing unrepaired side tissue located on at least one of anterior and posterior sides of the repaired rotator cuff with at least one flexible coupler to form a reconstructed rotator cuff with secured side tissue, wherein securing the unrepaired side tissue includes forming at least one suturing or stitched region along the repaired rotator cuff and by providing a plurality of suture passes over the unrepaired side tissue with the at least one flexible coupler.

2. The rotator cuff reconstruction method of claim 1, further comprising securing the unrepaired side tissue to bone without tying knots.

3. The rotator cuff reconstruction method of claim 1, further comprising attaching the at least one flexible coupler to the repaired rotator cuff and to at least another fixation device.

4. The rotator cuff reconstruction method of claim 3, further comprising attaching the at least one flexible coupler to a repair limb of the repaired rotator cuff.

5. The rotator cuff reconstruction method of claim 4, wherein the repair limb is a medial-lateral repair limb of the repaired rotator cuff.

6. The rotator cuff reconstruction method of claim 3, wherein the at least another fixation device is a knotless anchor.

7. The rotator cuff reconstruction method of claim 3, wherein the at least another fixation device is a knotted anchor.

8. The rotator cuff reconstruction method of claim 1, wherein the at least one flexible coupler is suture or suture tape.

9. The rotator cuff reconstruction method of claim 1, wherein the at least one suturing or stitched region extends along at least one dimension of the side tissue.

10. The rotator cuff reconstruction method of claim 1, further comprising providing a biological construct to reinforce the at least one suturing or stitched region.

11. The rotator cuff reconstruction method of claim 10, wherein the biological construct is graft, collagen, collagen patch or biological material.

12. The rotator cuff reconstruction method of claim 1, wherein the at least one flexible coupler is a combination of suture and suture tape.

* * * * *